(12) United States Patent
Denton

(10) Patent No.: US 7,389,947 B2
(45) Date of Patent: Jun. 24, 2008

(54) PUMP-BOTTLE ATOMIZER

(75) Inventor: Marshall T. Denton, Salt Lake City, UT (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 687 days.

(21) Appl. No.: 10/618,459

(22) Filed: Jul. 11, 2003

(65) Prior Publication Data
US 2005/0017088 A1   Jan. 27, 2005

(51) Int. Cl.
B05B 9/043 (2006.01)
(52) U.S. Cl. .................. 239/333; 239/546; 239/588; 239/602; 239/DIG. 12; 222/180; 222/321.1; 222/402.1; 222/527; 222/573; 248/75
(58) Field of Classification Search ............. 222/527, 222/530, 180, 181.1, 181.3, 529, 573, 321.1, 222/321.7, 321.9, 402.1, 537; 239/377, 345, 239/402.1, 333, 337, 519, 587.1, 546, 588, 239/602, DIG. 12; 220/737, 751, 758; 248/75
See application file for complete search history.

(56) References Cited

U.S. PATENT DOCUMENTS

| | | | | |
|---|---|---|---|---|
| 238,388 A | * | 3/1881 | Heine | 239/588 |
| 1,632,218 A | * | 6/1927 | Chaffin et al. | 222/385 |
| 2,192,415 A | * | 3/1940 | Schwarzenzer | 229/400 |
| 2,543,746 A | * | 3/1951 | Morrison | 221/307 |
| 2,968,441 A | * | 1/1961 | Holcomb | 239/588 |
| 3,402,741 A | * | 9/1968 | Yurdin | 138/118 |
| 3,653,556 A | * | 4/1972 | Moran et al. | 222/309 |
| 4,305,528 A | * | 12/1981 | Craig | 222/530 |
| 4,463,779 A | * | 8/1984 | Wink et al. | 138/125 |
| 4,664,300 A | * | 5/1987 | Strickland | 222/530 |
| 4,669,508 A | * | 6/1987 | Neaves | 138/121 |
| 5,176,654 A | * | 1/1993 | Schreiber | 604/181 |
| D333,000 S | | 2/1993 | Good et al. | |
| D338,064 S | * | 8/1993 | Jones et al. | D24/128 |
| D340,185 S | | 10/1993 | Martone | |
| D344,231 S | | 2/1994 | Gagnon | |
| 5,490,630 A | | 2/1996 | Hecker | |
| 5,503,306 A | * | 4/1996 | Knickerbocker | 222/321.1 |
| 5,511,538 A | | 4/1996 | Haber et al. | |
| 5,529,226 A | * | 6/1996 | Alberth, Jr. | 222/402.1 |
| 5,564,665 A | * | 10/1996 | Resnick | 248/519 |
| 5,573,039 A | * | 11/1996 | Mang | 138/141 |
| 5,601,077 A | | 2/1997 | Imbert | |
| 5,624,090 A | * | 4/1997 | Gammelgaard | 248/102 |
| 5,890,631 A | * | 4/1999 | Spurlock et al. | 222/527 |
| 5,988,530 A | * | 11/1999 | Rockefeller | 239/333 |
| 6,102,258 A | * | 8/2000 | Riley et al. | 222/543 |
| 6,105,620 A | * | 8/2000 | Haberl | 138/118 |

(Continued)

OTHER PUBLICATIONS

Official Gazette, p. 2224, Apr. 15, 1997.

(Continued)

*Primary Examiner*—Steven J Ganey
(74) *Attorney, Agent, or Firm*—TraskBritt

(57) ABSTRACT

A fluid atomizer that can include an orientable extension conduit between a pump bottle and an atomizing nozzle. A brace element between the bottle and the conduit limits movement of the nozzle during actuation of the pump mechanism. A resilient enlargement to engage the bottle may be included to permit suspending the bottle in commercially available storage racks.

11 Claims, 2 Drawing Sheets

U.S. PATENT DOCUMENTS

| | | | |
|---|---|---|---|
| 6,112,743 A | 9/2000 | Denton | |
| 6,253,971 B1 * | 7/2001 | Cobb | 222/402.1 |
| 6,325,237 B1 * | 12/2001 | Gish | 220/737 |
| 6,412,671 B1 * | 7/2002 | Riley et al. | 222/538 |
| 6,960,171 B2 * | 11/2005 | Sanders | 600/558 |

OTHER PUBLICATIONS

"Meeting the Challenge . . . ", *Valois Pharm.*, pp. 1-12.

* cited by examiner

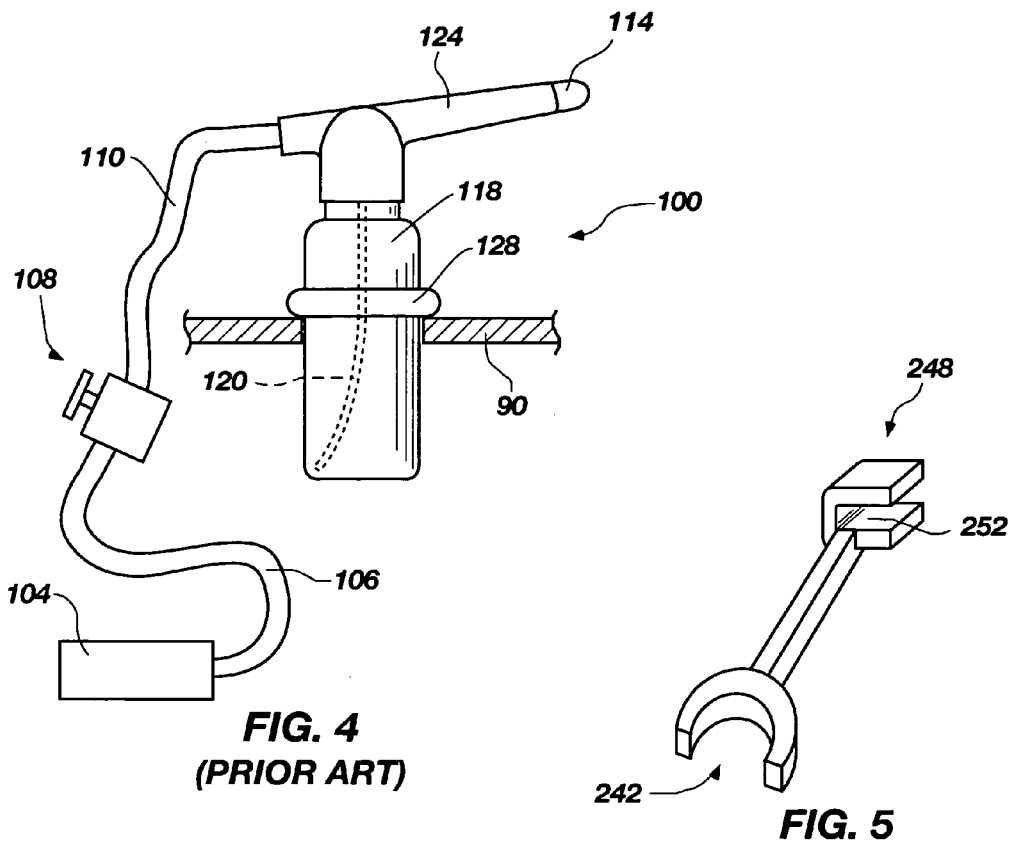
FIG. 4
(PRIOR ART)
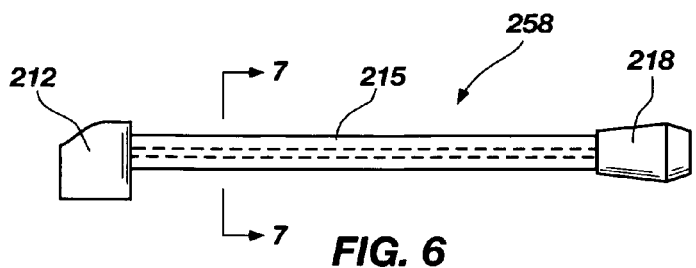
FIG. 5
FIG. 6
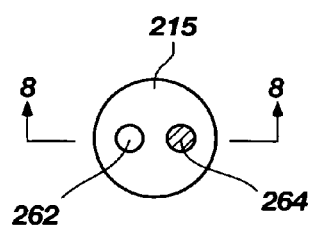
FIG. 7
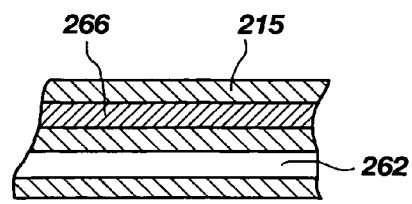
FIG. 8

PUMP-BOTTLE ATOMIZER

TECHNICAL FIELD

The invention relates to atomizing nozzles and devices which dispense fluids in a misted form. Certain devices constructed according to the instant invention are particularly suitable for use in nasal and oral medication therapy. One aspect of the invention resolves a bottle suspension problem.

BACKGROUND

A long and widely used atomizer is known as a "DeVilbiss atomizer". The DeVilbiss atomizer uses the Venturi principle to extract fluids from a reservoir for subsequent discharge through a nozzle as a mist. Such atomizers have support apparatus custom formed to accommodate a certain bottle shape. A concern in use of such atomizers is the possibility for unavoidable patient cross-contamination.

Positive pressure pump-bottle atomizers may prevent patient cross-contamination, but generally do not fit in the custom support apparatus ubiquitous in therapy rooms. Furthermore, operation of the pump mechanism can undesirably alter the point of impact of a discharge mist. Therefore, while attempting to treat a nostril, a therapist may accidentally squirt a patient in the eye, or cheek. In any event, when delivery of the treatment fluid is not well controlled, an over- or under-medicated state may occur in the patient.

DeVilbiss and pump-bottle atomizers require a fluid delivery line to stay below a fluid surface in a fluid reservoir. Consequently, manipulation of a direction of discharge from the nozzle may be limited. One attempt to increase control over a discharge direction is provided in a commercially available compact atomizer having a rotatable conduit section between a pump head and an atomizing nozzle. The conduit may be rotated to point the nozzle up, down, horizontally, or somewhere in-between. However, such an atomizer still lacks a desirably stable atomizer nozzle for control of the discharge impact site.

Co-pending application, Ser. No. 10/099,486, titled "MEDICAL ATOMIZER" and filed Mar. 15, 2002, discloses atomizer nozzles connectable to syringes for nasal and oral medication delivery. A deformable extension conduit between an atomizing nozzle and a syringe fluid source is disclosed in this reference.

BRIEF SUMMARY OF THE INVENTION

The invention can be embodied as an improved atomizer of the type in which a fluid housed inside a container is ejected through a nozzle. The improved atomizer includes a (typically cylindrical) bottle to hold the fluid. A resilient support structure adapted to engage a wall of the bottle at one or more locations along a bottle axis is included in some embodiments to permit suspension of the bottle by the support structure in a receiving socket or hole of a commercially available storage device. One workable resilient element provides a combined cross-section, through the resilient element and the bottle, having a size to permit suspension of the bottle by the resilient element on a rim of a socket of a commercially available storage device.

Preferred embodiments of the invention include an extension conduit between a pump mechanism and an atomizing nozzle. It is currently preferred that the conduit includes at least a distal portion that is malleable and deformable to permit orientation of a direction of discharge from the nozzle. The atomizer can include a brace with a first end adapted for engagement with the bottle, and a second end carrying structure adapted to engage the conduit at a location spaced apart distally from the pump mechanism. The brace desirably functions to resist movement of the nozzle during actuation of the pump mechanism.

Braces of certain atomizers can be configured for a first end of the brace to form, a clip-on or removable attachment to a portion of the bottle. Braces can also be permanently attached at their first end to a bottle. Structure carried at a second end of a brace is generally configured and arranged to hold a conduit. It is currently preferred for a brace to form a clip-on or removable attachment to the conduit. In any case, damping structure typically carried at the second end of the brace desirably is configured and arranged to resist motion, induced by the pump-mechanism, of a portion of the conduit distal to the damping structure.

A pump mechanism used in the instant invention typically includes a pump head that can be displaced by a human digit through a vertical distance between a first and a second elevation. One desirable brace, generally useful in atomizers according to the invention, can be configured and arranged to hold the conduit to provide a fulcrum location at a third elevation, with the third elevation being approximately midway between the first and the second elevations, thus reducing a horizontal displacement of the fulcrum during vertical actuation of the pump mechanism. It is also within contemplation that a proximal portion of the conduit, located between the pump head and structure carried at the second end of the brace, can be configured and arranged to reduce a horizontal deflection of the nozzle during actuation of said pump mechanism.

The invention can form a stabilized pump-bottle fluid atomizer. Such a stabilized atomizer typically includes a pump mechanism operable to pressurize a fluid contained in the pump-bottle. The pump mechanism generally includes a pump head displaceable by a human digit through a vertical distance between a first and a second elevation. Further included are a conduit between the pump head and a fluid atomizing nozzle, and a brace between the pump-bottle and the conduit. The brace desirably is configured and arranged to hold the conduit thus resisting motion of the nozzle during actuation of the pump mechanism. It is currently preferred for the conduit to include a distal portion that is deformable to orient a fluid discharge direction of the nozzle.

Exemplary braces are adapted for removable attachment to the conduit. Furthermore, the pump head is desirably adapted for removable attachment to the pump mechanism, thus permitting replacement of a low cost assembly comprising the pump head, the conduit, and the atomizing nozzle. The low cost assembly may be replaced between treatment of different patients to maintain sterility of the atomizer and prevent patient cross-contamination.

The invention can also be embodied as a pump-bottle fluid atomizer, including a bottle structured to hold a fluid, and a pump mechanism operable to pressurize the fluid in the bottle. One serviceable pump mechanism includes a pump head displaceable by a human digit through a vertical distance between a first and a second elevation. Such a pump-bottle fluid atomizer also typically includes a bendable conduit between the pump head and a fluid atomizing nozzle. The bendable conduit includes a malleable and deformable portion permitting user control over the orientation of a direction of discharge from the nozzle. The pump-bottle fluid atomizer can also include a brace, between the bottle and the conduit, operable to reduce motion of the nozzle during actuation of the pump mechanism.

BRIEF DESCRIPTION OF THE SEVERAL VIEWS OF THE DRAWINGS

In the drawings, which illustrate what are currently considered to be the best modes for carrying out the invention:

FIG. 4 is a side view in elevation of a prior art atomizer,

FIG. 5 is a view in perspective of one embodiment of brace structure, also illustrated in FIG. 1, according to the invention;

FIG. 6 is a currently preferred embodiment of the invention;

FIG. 7 is a cross-section view of a conduit illustrated in FIG. 6, taken through section 6-6 and looking in the direction of the arrows; and FIG. 8 is a cross-section view of the conduit illustrated in FIG. 7, taken through section 7-7 and looking in the direction of the arrows.

DETAILED DESCRIPTION OF THE ILLUSTRATED EMBODIMENTS

Figure 1:
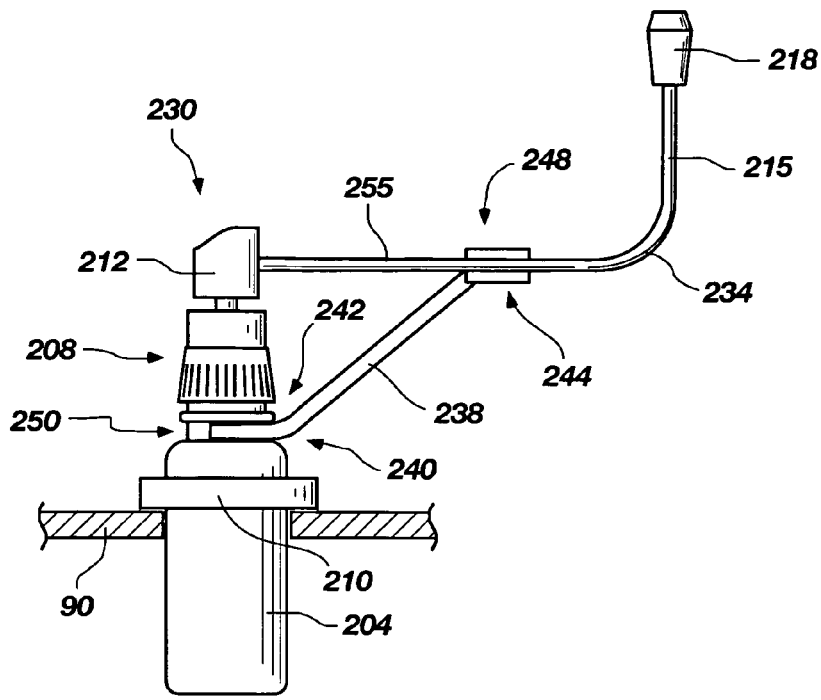
FIG. 1 is a side view of an embodiment of the invention.

A widely used, venturi-type atomizer, generally indicated at 100, is illustrated in FIG. 4. Atomizer 100 is known as a DeVilbiss atomizer, and is sold by Sunrise Medical HHG Inc., of Somerset, Pa. U.S.A. A DEVILBISS atomizer 100 typically requires a pressurized air source 104, connecting tubing 106, a valve 108, and more tubing 110. In use, a practitioner causes a fluid discharge from nozzle tip 114 by opening valve 108. Fluid contained in bottle 118 is drawn through suction line 120, passes along extended nozzle 124, and finally exits in misted form at tip 114.

Atomizers constructed according to atomizer 100 and illustrated in FIG. 4 have been long and widely used, and have spawned custom support apparatus constructed in correspondence with characteristics of bottle 118. One typical receiving structure 90 for an atomizer 100 provides a hole with a diameter sized to receive the bottom end of bottle 118. An enlarged portion of bottle 118 forms a bottle support 128 operable to suspend a bottle 118 from a rim of such a hole. While workable as a support structure, enlargement 128 increases the cost of an atomizer 100. Support structure 128 formed in the custom-shaped bottle 118 precludes use of a "normal" bottle, and fails to leverage mass manufacturing benefits.

One problem with atomizers, such as atomizer 100 which operates by harnessing pressure differentials created by a venturi nozzle, is the potential for patient cross-contamination. Fluid is removed from bottle 118 by suction, during which pressure inside the bottle 118 is lower than the atmospheric pressure outside the tip 114. When the discharge valve 108 is closed, suction is released, and the fluid in the suction line 120 returns toward the bottle 118 in a backwash action. Suction line 120 has a conduit connection (not illustrated) with an opening at tip 114. Touching a tip to a patient can contaminate the tip 114. Contaminants from tip 114 may then be drawn along with the fluid in suction line 120 to contaminate the fluid inside of bottle 118. This contamination problem is not solved by sterilizing a nozzle 124 and tip 114 between patients, because the fluid inside bottle 118, and any fluid remaining in line 120, carries the contaminant.

A second problem with such an atomizer 100 is the constraint imposed by the suction line 120 to maintain the bottle 118 in a substantially vertical orientation to keep an entrance to suction line 120 within the treatment fluid inside a bottle 118. Such a positioning constraint can make it difficult, or impossible, to direct a discharge from tip 114 to a desired area, particularly in treatment of a nasal area of a patient. In trying to direct a vertical discharge, a health practitioner is more likely to touch tip 114 to a patient's nasal area, thereby increasing risk of patient cross-contamination.

Figures 2, 3:
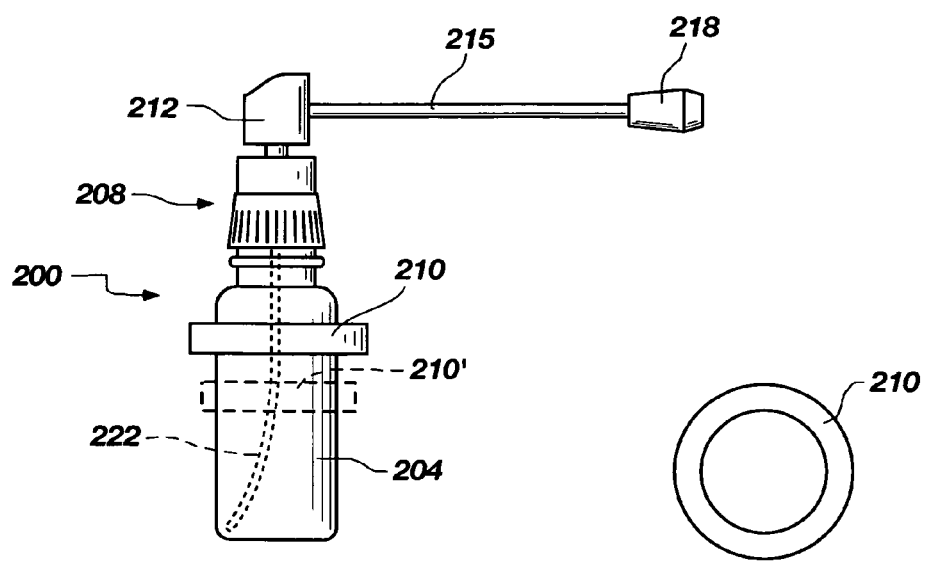
FIG. 2 is a side view of a second embodiment of the invention.
FIG. 3 is a top view of bottle enlargement structure illustrated in FIG. 2.

FIG. 2 illustrates one solution, embodied in a first currently preferred atomizer and generally indicated at 200, to both the bottle support and the cross-contamination problems inherent in an atomizer 100. Atomizer 200 uses a pump-bottle 204 and a pump mechanism, generally indicated at 208. The pump mechanism 208 is typically configured for operation by a human digit, e.g. a finger or a thumb. Operation of the pump mechanism 208 causes a positive pressure in the bottle 204 to force fluid flow through the atomizer 200.

Still with reference to FIG. 2, a suspension structure 210 may be installed on a commercially available "normal" bottle 204 to provide a bottle support workable in custom support apparatus designed to receive the bottle 118 of atomizer 100. A pump head 212 directs treatment fluid through extension conduit 215 for discharge as a mist through atomizer nozzle 218. Because the pump mechanism 208 uses positive pressure to cause fluid flow, no backwash action is possible, and the fluid inside bottle 204 remains sterile. A low cost assembly that can be sterilized, including pump head 212, conduit 215, and atomizer 218, can be replaced between treatment of different patients to completely eliminate patient cross-contamination.

FIG. 3 illustrates certain details of construction for one workable suspension structure 210 embodied as a resilient ring 210. A ring 210 generally has an inside diameter sized smaller than an outside diameter of a bottle 204. It should be realized that a ring 210 is also workable on bottles having cross-sections other than round, including square bottles. Forcing the ring 210 onto a bottle 204 causes a self-biased engagement between ring 210 and bottle 204. The ring 210 may therefore be positioned at a variety of locations (e.g., 210 or 210') along an axis of a bottle such as bottle 204.

Of course, a ring 210 can have a cross-section shape of any sort, including the illustrated substantially square shape. Alternative cross-section shapes include round, such as the cross-section found in a donut or an O-ring. In fact, O-rings of suitable large size are workable as support structure 210. However, one practical manufacturing method simply involves slicing axially short cross-sections from a resilient conduit, yielding the illustrated ring 210 with a substantially square cross-section. Suitable materials of construction for a ring 210 include rubber, urethane, plastics, polymers in general, and other such materials capable of forming a self-biased engagement with a bottle 204, or bottles having other shapes.

With reference again to FIG. 2, it is preferred for a conduit 215,to include a malleable and deformable portion to permit a user to define a bend in conduit 215 to aim a discharge direction from nozzle 218. However, even an extension conduit 215 formed substantially as a simple plastic straw is operable in certain embodiments of the invention. One advantage provided by an extension conduit 215 that is controllably deformable is that a nozzle 218 may be aimed in a vertical orientation for a substantially vertical discharge, e.g. into a patient's sinus area, while maintaining an entrance of suction line 222 within treatment fluid inside bottle 204. Furthermore, a nozzle 218 may be pointed for discharge in a desired direction while maintaining an atomizer 200 in a convenient orientation for actuation of the pump mechanism 208 by a health care practitioner.

FIG. 1 illustrates a second currently preferred embodiment of an atomizer, generally indicated at 230. At least a distal portion 234 of conduit 215 is malleable to permit a user to define a plurality of discharge directions of atomizing nozzle 218. As illustrated, the nozzle 218 has been oriented for a discharge directed in a substantially vertical direction. It should be noted that operation of pump mechanism 208 requires a displacement of pump head 212. Pump head 212 carries conduit 215 and atomizer 218. Moving pump head 212 can therefore cause a corresponding displacement of nozzle 218, which can undesirably move the point of impact of a discharge mist.

One solution to improve control over a point of impact of a discharge mist is also illustrated in FIG. 1, and is embodied as a brace 238. Brace 238 operates to resist motion of nozzle 218 relative to bottle 204. Since bottle 204 is held by a user's hand, it can remain substantially stationary while pump mechanism 208 is actuated. A first end 240 of brace 238 desirably carries attachment structure, generally indicated at 242, to couple a brace 238 to a bottle 204. A second end 244 of brace 238 carries attach structure, generally indicated at 248, operable to couple brace 238 to conduit 215. Currently preferred braces 238 are removable, at least at the second end 244, although such is not a requirement.

One convenient location for removable attachment of brace 238 to a bottle 204 is at bottle neck 250. As illustrated in FIGS. 1 and 5, bottle attach structure 242 may be formed as a resilient clip-on structure sized to engage bottle neck 250. Alternative construction for attach structure 242 is within contemplation, including a plate-like element having a through-hole with a diameter sized to receive a bottle neck 250. Since pump mechanism 208 typically can be unscrewed from bottle 204, the hole of such an alternative attach structure can be placed onto the bottle neck 250, and the pump mechanism can be screwed back into engagement with the bottle 204 to secure the plate-like structure and hold a first end 240 of brace 238 in engagement with a bottle 204.

A second end 244 of brace 238 carries attach structure 248 for coupling the brace 238 to a conduit 215. It is currently preferred that the attach structure 248 forms a removable coupling or connection. One such attach structure 248 is illustrated in FIGS. 1 and 5, and includes a channel 252 sized to receive a conduit 215. Channel 252 operates as a motion dampener for nozzle 218 and forms a clip-on attachment to conduit 215. Attach structure 248 operates as a fulcrum around which a proximal portion 255 of conduit 215 may bend, thereby stabilizing distal portion 234 from rotation and displacement during operation of pump mechanism 208. The removable coupling formed between illustrated brace 238 and conduit 215 permits easy replacement of a sterilizable assembly including pump head 212, conduit 215 and nozzle 218.

It is to be realized that a brace 238 may be embodied in many other forms, including simply as a relatively stiff wire, length of plastic or wood, or piece of metal. Embodied as a wire, a brace may be fastened on one end to a bottle 204, and fastened on the other end to a convenient location on conduit 215. An alternative fastening method may include wrapping the wire around a bottle or bottle neck, adhesively fixing the wire to a bottle, taping the wire to a bottle fixing a wire to a support structure such as ring 210, and shaping the wire to form, a clip-on attachment to the bottle. Similar attachment methods are workable to fasten a wire to a conduit. It is currently preferred to form a brace 238 by molding a polymer; such as by plastic injection molding.

FIG. 4 illustrates proximal portion 255 of conduit 215 in a horizontal orientation. It is preferred for such an orientation to occur at a mid-stroke position of pump head 212. The up-and-down displacement of head 212 then follows a base of an equilateral triangle, with a fulcrum formed by attach structure 248 at an apex of the triangle. Assuming a substantially fixed connection between conduit 215 and attach structure 248, the illustrated orientation therefore minimizes a required horizontal deflection of attach structure 248 to accommodate the vertical motion of a pump stroke. As an alternative, or even additional measure, proximal end 255 of conduit 215 can be bent, or formed in some nonlinear shape, to permit its extension and contraction (bending and unbending, to act as a spring element), to reduce or eliminate a corresponding horizontal motion of attach structure 248 (and consequently nozzle 218), during vertical displacement of the pump head 212.

FIG. 6 illustrates a currently preferred assembly, generally indicated at 258, forming a disposable and sterilizable atomizer nozzle for a pump-bottle atomizer, such as atomizer 230. Assembly 258 includes a pump head 212, a deformable extension conduit 215, and an atomizing nozzle 218. The constituent parts are typically manufactured from medical grade materials, including plastics and other polymers.

The conduit 215 can be embodied as a multilumen conduit, as illustrated in FIGS. 7 and 8. One lumen 262 provides fluid flow communication for treatment fluids between pump head 212 and nozzle 218. Another lumen 264 houses a deformable length of metal wire 266. Wire 266 desirably will hold a deformed shape and maintain the deformed shape in conduit 215. It is currently preferred for wire 266 to occupy at least a portion of the length of conduit 215. Furthermore, wire 266 desirably is located in distal portion 234 to permit a user to control a direction of discharge from nozzle 218.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An improved atomizer of the type in which a fluid housed inside a container is ejected through a nozzle, the improvement comprising:
    a bottle operable as the container to hold the fluid, the bottle comprising a generally cylindrical portion;
    a resilient element structured to form a self-biased engagement with a wall of the cylindrical portion of the bottle at a plurality of locations along an axis of the bottle, the resilient element having a size larger than the cylindrical portion of the bottle so as to permit suspension of the bottle by the resilient element, in a receiving socket of a storage device; and
    an extension conduit between a pump mechanism and an atomizing nozzle, said conduit being malleable and deformable to permit a user to adjust the orientation of a direction of discharge from said nozzle, wherein the improved atomizer is in combination with
    a brace with a first end adapted for engagement with the bottle, and a second end carrying structure adapted to engage the conduit at a location spaced apart distally from the pump mechanism, the brace being operable to resist movement of the nozzle during actuation of the pump mechanism.

2. The improved atomizer of claim 1, wherein:
the first end of said brace is configured and arranged to form a clip-on attachment to a portion of said bottle.

3. The improved atomizer of claim 1, wherein:
the second end of said brace is configured and arranged to form a clip-on attachment to said conduit.

4. The improved atomizer of claim 1, wherein:
a damping structure carried at the second end of said brace is configured and arranged to resist motion, induced by said pump-mechanism, of a portion of said conduit distal to said damping structure.

5. The improved atomizer of claim 1, wherein:
said pump mechanism comprises a pump head displaceable by a human digit through a vertical distance between a first and a second elevation; and
said brace is configured and arranged to hold said conduit to provide a fulcrum location at a third elevation, said third elevation being approximately midway between said first and said second elevations, so as to reduce a horizontal displacement of the fulcrum during vertical actuation of said pump mechanism.

6. A stabilized pump-bottle fluid atomizer, comprising:
a pump mechanism operable to pressurize and eject fluid from confinement inside a pump-bottle, the pump mechanism comprising a pump head displaceable by a human digit through a vertical distance between a first and a second elevation;
a conduit between the pump head and a fluid atomizing nozzle; and
a brace between the pump-bottle and the conduit, the brace being configured and arranged to hold the conduit so as to resist motion of said atomizing nozzle during actuation of said pump mechanism, wherein:
a structure carried by said brace is adapted to provide a fulcrum location for localized bending of said conduit at a third elevation, said third elevation being approximately midway between said first and said second elevations so as to reduce a horizontal displacement of the fulcrum during vertical actuation of said pump mechanism.

7. A stabilized pump-bottle fluid atomizer comprising:
a pump mechanism operable to pressurize and eject fluid from confinement inside a pump-bottle, the pump mechanism comprising a pump head displaceable by a human digit through a vertical distance between a first and a second elevation;
a conduit between the pump head and a fluid atomizing nozzle;
a brace between the pump-bottle and the conduit, the brace being configured and arranged to hold the conduit so as to resist motion of the atomizing nozzle during actuation of the pump mechanism, and
a resilient element adapted to engage a wall of a cylindrical portion of the pump-bottle at a plurality of locations along an axis of the pump-bottle, the resilient element having a diameter larger than the cylindrical portion of the pump-bottle so as to permit suspension of the pump-bottle by the resilient element in a socket of a storage device wherein:
said pump head is adapted for removable attachment to said pump mechanism, so as to permit replacement of a unitary assembly comprising said pump head, the conduit, and said atomizing nozzle.

8. A pump-bottle fluid atomizer, comprising:
a bottle structured to hold a fluid;
a pump mechanism operable to pressurize and eject fluid from confinement inside the bottle, the pump mechanism comprising a pump head displaceable by a human digit through a vertical distance between a first and a second elevation;
a conduit between the pump head and a fluid atomizing nozzle, the conduit comprising a malleable and deformable portion permitting a user to adjust the orientation of a direction of discharge from the atomizing nozzle;
a brace between the bottle and the conduit, the brace being operable to reduce motion of the atomizing nozzle during actuation of the pump mechanism, wherein:
the brace comprises first and second ends;
the first end being adapted for attachment to the bottle; and
the second end being adapted for removable attachment to the conduit at a location spaced apart distally from the pump head; and
said brace is configured and arranged to produce a fulcrum about which said conduit may bend so as to allow a vertical deflection of a proximal portion of said conduit and accommodate actuation of said pump mechanism; the fulcrum being located at a third elevation approximately midway between said first and second elevations to reduce a horizontal motion induced in the fulcrum by the vertical deflection of said proximal portion of said conduit.

9. The pump-bottle fluid atomizer of claim 8, wherein:
the second end of said brace is configured and arranged to form a clip-on attachment to a portion of said conduit between said pump head and said atomizing nozzle.

10. The pump-bottle fluid atomizer of claim 8, wherein:
a proximal portion of said conduit, located between said pump head and structure carried at the second end of said brace, is configured and arranged to reduce a horizontal deflection of said nozzle atomizing during actuation of said pump mechanism.

11. The pump-bottle fluid atomizer of claim 8, further comprising:
a resilient element adapted to engage a wall of said bottle at one or more locations along an axis of said bottle, a combined cross-section of said resilient element and said wall having a size to permit suspension of said bottle by said resilient element in a socket of a commercially available storage device.

* * * * *